United States Patent [19]

Kornberg et al.

[11] Patent Number: 5,084,032

[45] Date of Patent: Jan. 28, 1992

[54] METHOD FOR USING A PROTECTIVE SHEATH IN AN INTRAVENOUS ASSEMBLY

[76] Inventors: Elliot Kornberg, 1980 N. Atlantic Ave. (Ste. 416), Cocoa Beach, Fla. 32931; William R. Tarello, 4875 Battery La. #304, Bethesda, Md. 20814

[21] Appl. No.: 508,721

[22] Filed: Apr. 16, 1990

Related U.S. Application Data

[63] Continuation-in-part of Ser. No. 546,491, Mar. 6, 1990, abandoned, which is a continuation-in-part of Ser. No. 372,016, Jun. 27, 1989, abandoned.

[51] Int. Cl.$^5$ .................................................. A61M 5/00
[52] U.S. Cl. ...................................... 604/263; 604/192
[58] Field of Search ................ 604/179, 180, 192, 198, 604/263, 283, 905; 128/917, 919

[56] References Cited

U.S. PATENT DOCUMENTS

| | | | |
|---|---|---|---|
| 1,522,198 | 1/1925 | Marcy | 604/192 |
| 3,434,473 | 3/1969 | Smith . | |
| 3,887,937 | 6/1975 | Bobo et al. . | |
| 4,005,710 | 2/1977 | Zeddies et al. . | |
| 4,112,944 | 9/1978 | Williams . | |
| 4,121,585 | 10/1978 | Becker, Jr. . | |
| 4,232,669 | 11/1980 | Nithske . | |
| 4,392,499 | 7/1983 | Towse . | |
| 4,419,098 | 12/1983 | Bennett . | |
| 4,752,292 | 6/1988 | Lopez et al. . | |
| 4,799,927 | 1/1989 | Davis et al. . | |
| 4,810,248 | 3/1989 | Masters et al. | 604/263 |
| 4,834,716 | 5/1989 | Ogle, II . | |
| 4,840,619 | 6/1989 | Hughes | 604/192 |
| 4,857,060 | 8/1989 | Rosenberg . | |
| 4,932,944 | 6/1990 | Jagger et al. | 604/191 |
| 4,998,922 | 3/1991 | Kuracina et al. | 604/192 |
| 5,011,475 | 4/1991 | Olson | 604/192 |

*Primary Examiner*—John D. Yasko
*Assistant Examiner*—Anthony Gutowski
*Attorney, Agent, or Firm*—Beveridge, DeGrandi & Weilacher

[57] ABSTRACT

A method of using a protective apparatus with an intravenous system and especially an implanted intravenous needle assembly or a Y-junction of a piggy back intravenous system. The protective apparatus includes a protective sheath having an open end and a second end suitable for connection with a fluid introduction source. The sheath includes a slot along its lowest surface and can include a needle extending within a hollow interior defined by the sheath. The sheath features two curved runner sections or a pair of wing-shaped runners which extend from a channel section defining a portion of the slot. The curved runner sections and wing-shaped runners allow for easy insertion of a needle into a taped receptive port of an implanted intravenous needle assembly. An alternate embodiment features two slits with or without an additional channel/elongated aperture combination. The two slits allow for easy insertion of a needle into a taped receptive port while the channel/elongated aperture combination allows for use of the protective sheath with a Y-junction of an intravenous system. An additional embodiment features a needle assembly with protective guard that can be easily connected within the interior of the protective sheath.

1 Claim, 11 Drawing Sheets

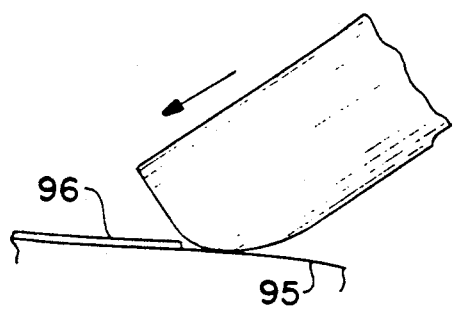
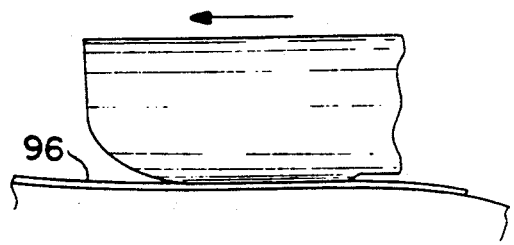
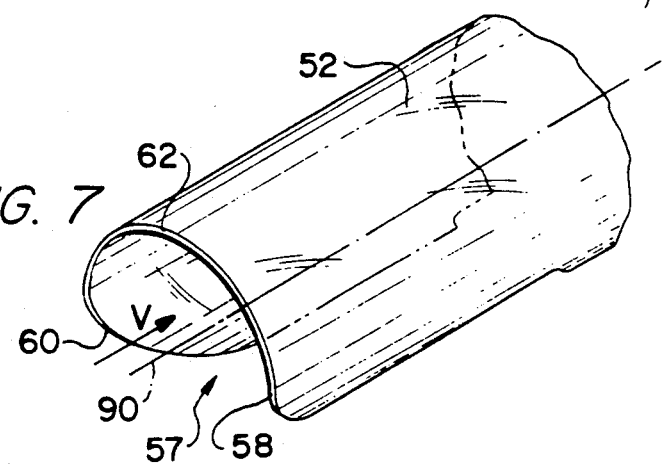
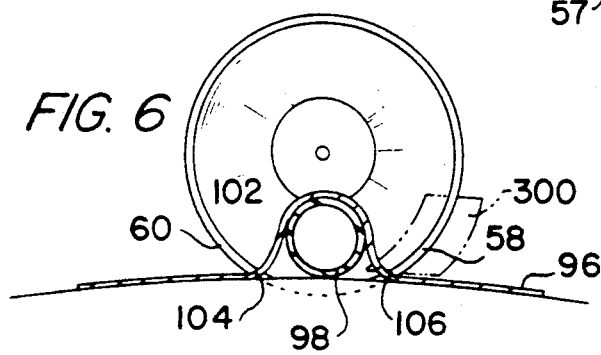
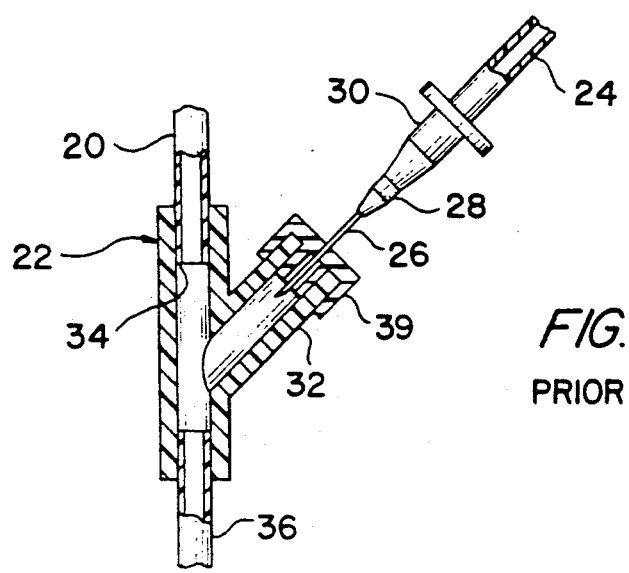
FIG. 8 PRIOR ART

METHOD FOR USING A PROTECTIVE SHEATH IN AN INTRAVENOUS ASSEMBLY

REFERENCE TO EARLIER APPLICATION

This application is a continuation-in-part of application Ser. No. 07-546,491 filed Mar. 6, 1990, now abandoned, which is a continuation-in-part of U.S. application Ser. No. 07/372,016 filed June 27, 1989, now abandoned.

BACKGROUND OF THE INVENTION

1. Field of the Invention

This invention relates to a protective shield for protection against needle contamination and accidental needle puncture. More particularly, this invention relates to a protective shield for protection against a needle which is inserted into an implanted intravenous cannula assembly or an auxiliary branch of a piggy back intravenous system.

2. Background Discussion

Intravenous systems are commonly used in treating patients with highly contagious diseases such as AIDs and hepatitis. The intravenous systems frequently include an implanted cannula assembly which, when the intravenous system is used on a human, is inserted in the upper surface of the hand or in some other convenient location. The implanted cannula assembly usually includes a flexible conduit extending below the skin together with a reception port above the surface of the skin. The reception port provides a location at which a fluid introduction device, such as a syringe or the end of an intravenous tube, is attached. The reception port is designed for easy removal of the intravenous tube so as to free the intravenous source from the patient for the purposes of providing a heparin flush, changing the intravenous fluid, easy movement of the patient, etc.

In the situations where a cannula is inserted in the reception port to inject a fluid (e.g. a heparin flush), the operator is subjected to the possibility of being stuck by the needle as the cannula is being manipulated for insertion into the reception port. There is also the chance of being stuck by a cannula when removing or replacing the cannula. Thus, medical personnel and, as is becoming more common today, family members in the case of home therapy and the like treating outpatients are susceptible to being stuck and being infected. Also, even if medical personnel or those people assisting outpatients are not infected, expensive tests and regulatory reports are required each time a person is stuck just to determine and record whether or not that person has been infected.

The intravenous tubing systems commonly used today also frequently include a piggy-back arrangement which comprises a fluid line connected to a patient at one end and to a bag or bottle of the opposite end. A Y-site or Y-junction is placed or formed in the fluid line. The Y-junction includes an auxiliary branch which is either connected to an auxiliary line and intravenous fluid source or, alternatively, provides a location for the injection of fluid with a syringe.

In utilizing such intravenous tubing systems, it is often required that a person helping the patient insert a needle into the auxiliary branch or remove a needle previously inserted. The person, removing the needle from the auxiliary branch or inserting the needle, is placed in jeopardy of being stuck or contaminated by coming into contact with an infected needle. Once the needle is removed, there also exists the possibility of medical personnel loosing grip of the auxiliary line and needle and dropping the needle. This creates not only the problem of fluid spattering but also increases the potential for medical personnel being stuck or scratched by the needle.

U.S. Pat. No. 4,752,292 to Lopez et al. discloses one solution to the problem of having medical personnel becoming contaminated by a needle previously inserted into the auxiliary branch of an intravenous tubing system. Lopez et al. feature an elongated cylindrical connector which surrounds the auxiliary branch needle and is designed for locking connection with the free end of the auxiliary branch of the piggy back intravenous system. The invention of Lopez et al., however, requires that the auxiliary branch of the piggy back intravenous system be specially designed for connection with the elongated cylinder encompassing the needle. Accordingly, the auxiliary line connector of Lopez et al. can only be used with a restrictive class of piggy back systems. Namely, a piggy back system utilizing an auxiliary branch specially designed for connection with the Lopez et al. elongated cylinder and associated attachment means.

Moreover, the rather complicated attachment means relied on in Lopez et al. present manufacturing problems as well as an increased chance of component failure.

SUMMARY OF THE INVENTION

The present invention is directed at providing, among other things, a protective shield which protects people from becoming contaminated by a cannula or needle being inserted or removed from both an implanted cannula assembly or an auxiliary branch of a piggy back intravenous system. The present invention is well suited for adaptation with implanted cannula systems and piggy back intravenous systems. The present invention avoids the restrictive nature of some of the prior art needle covering devices. In addition, the present invention avoids the prior art problems of expensive manufacturing requirements and increased failure possibilities. The present invention also represents a relatively inexpensive device which can be discarded after use or, if desired, formed of a material suitable for reuse.

In achieving the above advantages over the prior art, the present invention features a first embodiment of the protective apparatus designed for use with an implanted intravenous cannula assembly. The protective apparatus includes a protective sheath preferably formed of an essentially transparent plastic material of the polyolefin family such as polycarbonate or a more flexible material such as polypropelene, polyethylene, etc. The protective sheath comprises an upper portion, a lower portion, a connecting end, a hollow interior and an open end. The sheath is elongated and generally cylindrical. The dimensions of the protective sheath are such that the sheath can be inserted over the free end of the implanted intravenous cannula assembly.

The sheath features an elongated slot formed along its lower portion which originates at the open end of the sheath and extends towards the connecting end. At the open end, the sheath features two wing sections which preferably are formed during a molding process or subsequently by folding portions of the sheath outwardly. The wing sections extend outwardly about a line sloping upwardly from the lower portion to the upper portion. The wing sections provide a planar forward runner surface on each side of the open end of the sheath which allows the sheath to be easily insertable over strips of tape used to fasten in place the implanted cannula assembly.

The wing sections preferably represent about a third of the entire longitudinal length of the slot. The sloping lines defining the folding edge of the wing sections preferably extend toward the open end of the sheath such that the end of each sloping lines lies within the upper portion of the sheath. More preferably, the end of each of the sloping lines lies within the upper portion and within the mid-third of the upper portion. In this way, the wing sections define a gradually sloping smooth, planar surface which allows for the easy insertion of the sheath into place with respect to the reception port of the implanted cannula. The angle that the line slopes upwardly is preferably between 25° to 45°.

The slot further includes a channel section extending towards the connecting end and, in a preferred embodiment, an elliptical or elongated aperture into which the channel opens. In a preferred embodiment the channel section and elongated aperture are about equal in length.

The first embodiment can also be used to protect a person from being stuck by a cannula when the cannula is being inserted or removed from the auxiliary branch of an intravenous system containing a Y-site. The channel of the protective sheath has a width which is smaller than the diameter of the main fluid line in the intravenous system while the elliptical or elongated aperture has a transverse width equal to or larger than the main line. With this arrangement, the main line and/or the sheath deforms while the main line slides within the channel during insertion of the cannula into the auxiliary branch. The main line then becomes releasably locked within the aperture once it slides completely through the channel and the cannula is received within the auxiliary branch.

The cannula is preferably designed so as to extend beyond the mid-region of the sheath but before the open end. In the most preferred embodiment, the tip of the needle extends outwardly to the mid-region of the slot channel and before the wing sections such that an operator is unable to insert a finger into the open end of the sheath and into contact with the cannula.

In a second embodiment of the invention, the sheath features an elongated slot which originates at the open end of the sheath and extends towards the connecting end of the sheath. The slot formed in the sheath is defined by an edge which includes a pair of curved sections originating at the upper portion of the sheath and extending on opposite sides of the central axis of the sheath and downwardly to the lower portion. The edge further defines a channel region that has two sides which extend in essentially planar fashion from the lowermost portion of the pair of curved sections towards but not all the way to the connecting end. In a preferred embodiment the slot extends over about 75% of the entire length of the protective sheath.

The slot also preferably includes an elongated (e.g. somewhat elliptical) aperture which opens into the channel at the end of the channel furthest from the sheath's open end. The elongated aperture preferably represents 40 to 50% of the entire length of the slot. The aperture is dimensioned to have a transverse width which is equal to or greater than the main line of an intravenous fluid system. All of the channel, or a portion of the channel, is dimensioned so as to have a width which is less than the diameter of the main line to be inserted in the aperture. Hence, when the main line is being slid along the channel, deformation of either the main line itself or, when the sheath is formed of flexible material, the sheath, deforms and then snaps back in place once the object is inserted in the aperture.

The pair of curved sections which extend both downwardly and towards the connecting end of the sheath, are designed so as to be in a mirror image arrangement with one another and equally spaced from the central axis of the protective sheath. The edge defining the curved sections is advantageously designed so as to provide a planar surface along the entire length of the curved sections. In other words, the edge defining the curved sections presents a planar surface which is transverse to the line of sight when looking directly at the open end towards the connecting end. In this way, a pair of sleigh-like runners are provided. The advantages associated with these sleigh-like runners of the curved sections will become apparent in the description of the operation appearing below.

The connecting end of the protective sheath in each of the above-described embodiments includes a neck extension which receives connecting means suitable for attachment with a fluid insertion device such as the distal end of an intravenous tube or the forward end of a syringe casing. The connecting means preferably includes a cylindrical extension which is received within the neck extension of the protective sheath. Attached to, or integrally formed with, the cylindrical extension is a cup-shaped receiving member which diverges outwardly away from the protective sheath so as to provide a tapering internal recess. Extending peripherally about the outer end of cup-shaped member is a flange suitable for entering into a locking arrangement (e.g. a luer locking arrangement) with another member having a slotted recess dimensioned to receive the flange.

In a preferred embodiment, a cannula is attached at one end within a recess formed in the cylindrical extension of the connecting means. Attachment of the cannula to the recess formed in the cylindrical extension is preferably by way of adhesion and it has also been found to be advantageous to form the recess of the cylindrical extension with a plurality of projections axially spaced and extending inwardly so as to form pockets therebetween. The projections are dimensioned so as to come in contact with the exterior of the cannula while the pockets provide a good location for the pooling of adhesive. The free end of the cannula extends towards the open end of the protective sheath so as to be positioned within the hollow interior of the protective sheath. Preferably the cannula extends for about 40-75% of the entire length of the sheath.

When a needle or cannula is to be inserted into the receptive port of an implanted intravenous cannula assembly, the protective apparatus is connected to a fluid insertion device at its connecting end. In the typical situation, the implanted intravenous cannula assembly is taped on to the upper portion of the patient's hand. The use of tape would normally present a problem in attempting to slide a protective sheath over a portion of the implanted intravenous cannula assembly. However, the wing sections of the first described embodiment or the sleigh-like runners of the second embodiment, together with the slot, enable an operator to slide the lower portion of the protective sheath along the surface of the patient's hand as well as over the tape without disturbing the adhesion of the tape to the patient's hand. It has been found advantageous to form the edge defining the sleigh-like runners and the wing sections as a smooth, planar surface. The planar surface of the sleigh-like runners and the planar surface of the wing sections are thus free to easily slide along the patient's hand and over and along the tape which, when placed over the implanted intravenous cannula assembly, includes an tent-shaped cross section which would normally be easily disturbed were it not for the design of the present invention. The present invention thus enables a person to easily slide a needle into the reception port of an implanted intravenous cannula assembly without having to worry about being stuck and infected.

The second embodiment of the present invention can also be used as a protective sheath for protecting a person inserting a cannula into the auxiliary branch of an intravenous system. In utilizing the above-described embodiment in this manner, the slot is aligned so as to place the main line within the channel as the sheath is inserted over the auxiliary branch. Upon insertion of the protective sheath over the auxiliary branch, the needle is inserted into the receptive port of the auxiliary branch and the channel portion of the protective sheath slides past the main line branch until the main line branch is received within the aperture positioned at the end of the channel in the protective sheath.

In a third embodiment of the present invention, there is featured a protective apparatus which includes a protective sheath designed for use at the Y-junction of an intravenous assembly. As in the second embodiment, the third embodiment features a protective sheath having a connecting end, an open end, as well as a key-hole shaped slot which includes a channel section that opens into an elongated aperture formed at one end of the channel section. The third embodiment also features connecting means similar to that of the first embodiment along with a cannula. The cannula is preferably integrally connected to the connecting means such that the protective sheath surrounds and protects one from coming into contact with the pointed end of the cannula. The open end of the main body is dimensioned so as to enable one to insert the protective sheath over the auxiliary branch extension of the intravenous system such that the cannula can be inserted into the receptive port forming part of the auxiliary branch.

The key-hole shaped slot formed in the protective sheath is dimensioned such that the protective sheath can be slid past the main line by aligning the channel with the main line and forcing the main line through the channel and into the aperture formed at the end of the channel. The channel is dimensioned such that at least a section thereof has a width which is slightly less than the diameter of the main line. The aperture is dimensioned so as to have a transverse width which is essentially the same or slightly larger than the circumference of the main line.

In a preferred embodiment, a protective sheath is formed of a flexible material such that when the main line slides through the channel, the protective sheath deforms and then snaps back into place once the main line is received within the aperture formed at the end of the channel. In this way, the main line is releasably locked within the aperture and the snapping function also helps in letting the operator know that the protective sheath and cannula are in the proper position. Alternatively, the protective sheath can be formed of a relatively stiff material and the fluid line itself can provide the greater degree of deformation so as to releasably lock the line within the elongated aperture forming part of the slot.

Another embodiment of the present invention includes a protective sheath having an upper section, a lower section and two slits extending longitudinally between the upper and lower sections. The slits are arranged so as to receive therein tent-shaped strips of tapes when the protective sheath is being inserted over the reception port of an implanted intravenous cannula assembly. The slits are designed to have smoothly curving open edges and, in a preferred embodiment, tapering inlet sections.

To provide for use with an auxiliary branch, the slit in the above described embodiment is widened to have a width which is greater than the oppositely positioned slit. Also, the widened slit can be formed so as to have a channel section which opens into an elongated aperture similar to the embodiments described above.

Alternatively, a channel and aperture can be formed in the addition to the pair of opposed slits. The channel and aperture combination provides for easy insertion over an auxiliary branch of a y-junction. Also, the channel and aperture combination helps in enabling the user to look through and visually determine the proper alignment of the slits into which the tape strips are inserted when the device is used with an implanted intravenous cannula assembly. Moreover, the added channel/aperture combination can itself be used in combination with one of the slits to provide a location where the tent-shaped portion of the tape is to be inserted.

Connection means, formed at the ends of each of the above-described protective sheaths, includes a cup-shaped member with a tapered port or recess for locking engagement with a fluid insertion device. The connections means further includes a projection member having a recess which receives one end of a cannula in fixed relationship.

The preferred manner of securing the connecting means to the protective sheath includes ultrasonically welding the tapering exterior of the cup shaped member to a neck extension formed at one end of the protective sheath, ultrasonically welding the neck extension to the projection member attached to the cannula, and forming the cup-shaped member, projection member and protective sheath as a single integrally molded article. In the latter arrangement the cannula can be insert molded with respect to a recess provided in the projection member and/or adhered to the projection member.

Yet another embodiment of the present invention features a cannula assembly comprising a flanged hub and a cannula secured to the hub and extending out away from the hub. The interior of the protective sheath is provided with locking grooves to receive the flanged hub. Also, the projection member, forming part of the connecting means, includes a tapering extension which is tapered so as to be received by a tapering recess formed in the hub. The cannula assembly is thus releasably and yet securely retained by the combination of (1) the projection member extending into the hub recess and (2) the hub flange received by the locking grooves.

A protective guard is also provided to make it easier for insertion of the needle into locking position. The protective guard represents an elongated cigar shaped member which is releasably attached at its one open end to the hub of the cannula assembly. For example, longitudinal grooves can be formed in the hub exterior and complimentary projections enable a twisting action as well as longitudinal separation.

In operation, the protective guard with attached hub assembly is inserted into the open end of the protective sheath and, through a twisting action, the cannula assembly is fixed in place with respect to the protective sheath. The protective guard is then disconnected from the cannula assembly by drawing the guard away from the fixed cannula assembly.

The protective sheaths described in the above embodiments is preferably formed of a material within the family of polyolefins such as polycarbonate or other suitable plastics which are somewhat flexible. For the purposes of this invention, polycarbonate has proven most suitable as it is well adapted to maintaining its transparency after being sterilized by ultra violet rays.

An additional embodiment of the invention features a flap either integrally formed with the protective sheath or securely attached at one end to the protective sheath on one side of the channel formed therein. The flap is of a length sufficient to extend across the elongated channel and come into attachment with the protective sheath on the opposite side. At the free end of the flap is provided a securement device such as an adhesive patch which can be joined to the exterior of the protective sheath on the opposite side of the channel. Alternatively, the adhesive patch can be formed on the exterior of the protective sheath and positioned such as to receive the flap in a locking arrangement when extended across the channel. An additional manner of attachment could include the use of plastic and loop patches (e.g., VELCRO patches) positioned on the exterior of the protective sheath and on the flap such that one patch can be attached to the other when the flap extends across the channel. The releasably lockable flap feature of the invention helps to further ensure that the protective sheath remains in proper position.

Additional features will become more fully apparent in the following description of the embodiments of this invention and from the appended claims.

BRIEF DESCRIPTION OF THE DRAWINGS

FIGS. 5A and 5B show the relationship between runner sections of the present invention and the underlying tape surface as the present invention is placed into the position shown in FIG. 4;

FIG. 6 illustrates a view looking into the open end of the present invention as well as the arrangement of the runners with respect to the underlying tape surface;

FIG. 7 shows a perspective view of a cut-away portion of the present invention;

FIG. 8 shows a prior art intravenous Y-junction;

DESCRIPTION OF THE PREFERRED EMBODIMENTS

Figure 13:
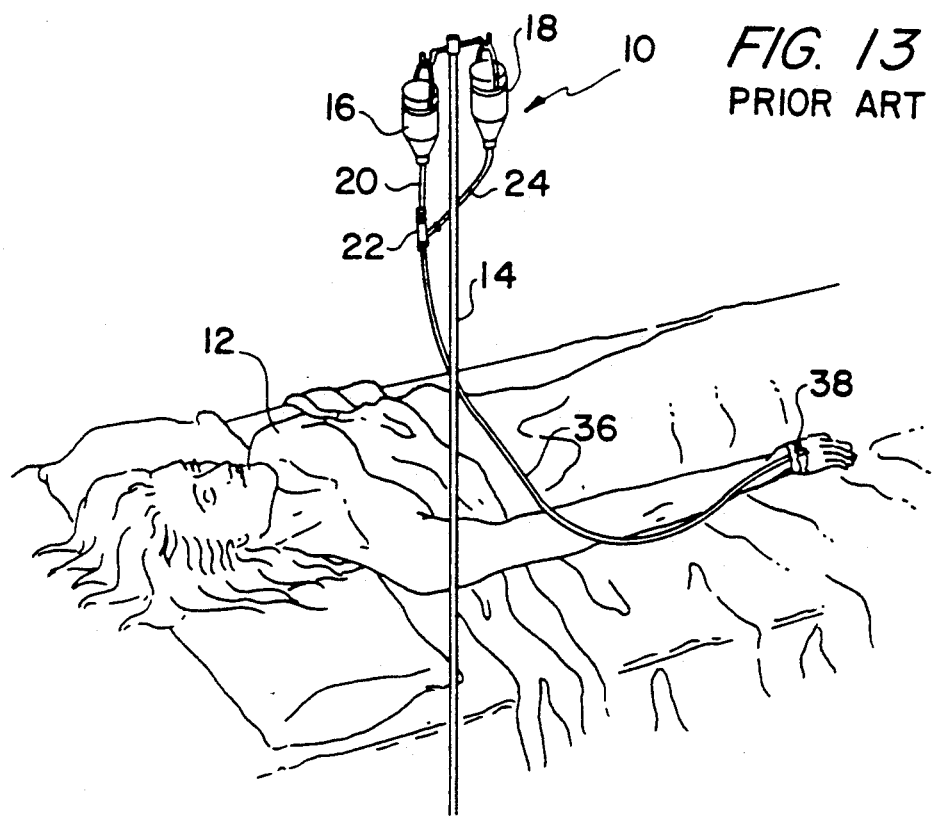
FIG. 13 shows a prior art illustration of an intravenous system attached to a patient.

FIG. 13 depicts a prior art piggy back intravenous system 10 being used in the treatment of patient 12. Piggy back intravenous system 10 features stand 14 supporting main fluid source 16 as well as auxiliary fluid source 18. A main line 20 extends from main fluid source 16 down towards Y-junction 22. Auxiliary line 24 extends down from its point of connection with auxiliary fluid source 18. At the end of auxiliary line 24 is positioned a needle or cannula 26 (FIG. 8) having at its end needle hub 28. As shown in FIG. 8, needle hub 28 is secured to adaptor 30 forming part of auxiliary line 24. Y-junction 22 is comprised of auxiliary branch 32 and main branch 34 which come together at a point above mixed fluid line 36. Mixed fluid line 36 has cannula 38 imbedded in the upper surface of the patient's hand and taped in position. FIG. 8 further shows auxiliary branch 32 having cup 39 through which needle 26 is inserted with cup 29 providing a sealing function.

A person removing or inserting needle 26 or 38 is faced with the possibility of becoming contaminated by being stuck or scratched by the needle.

Figure 1A:
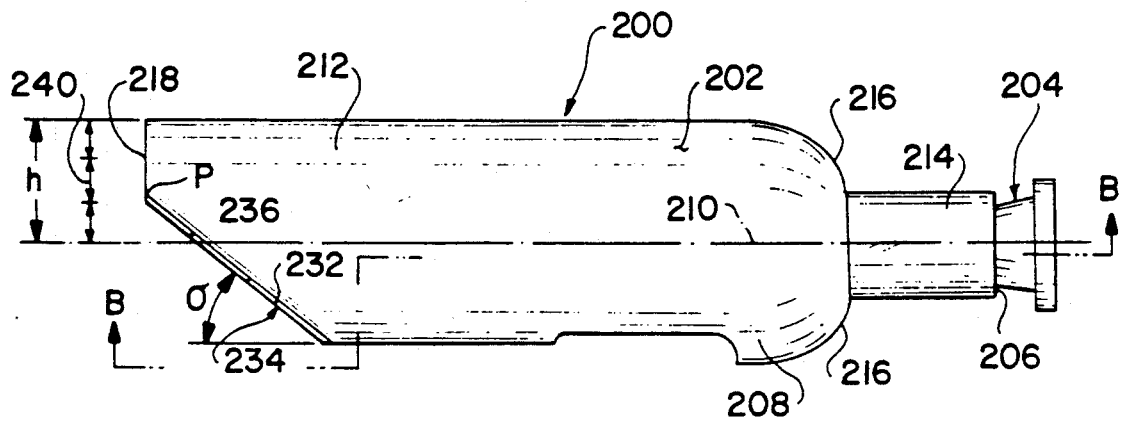
FIG. 1A shows a side view of a first embodiment of the present invention.

FIG. 1A shows, in side view, a first embodiment of the present invention featuring protective apparatus 200 which comprises protective sheath 202 and connecting means 204 secured to connecting end 206 of sheath 202.

Protective sheath 202 is preferably formed of a clear or translucent plastic material such as polyethylene, polypropelene or polycarbonate. Sheath 202 includes lower portion 208 which represents that portion of the sheath which lies below a horizontal plane lying on center line 210. Upper portion 212 represents that portion of the sheath which lies above said horizontal plane.

Protective sheath 202 further includes neck-extension 214 within which connecting means 204 is secured. As shown, sheath 202 is generally cylindrical in shape and has curved end portion 216 from which neck extension 214 projects outwardly.

Figure 1B:
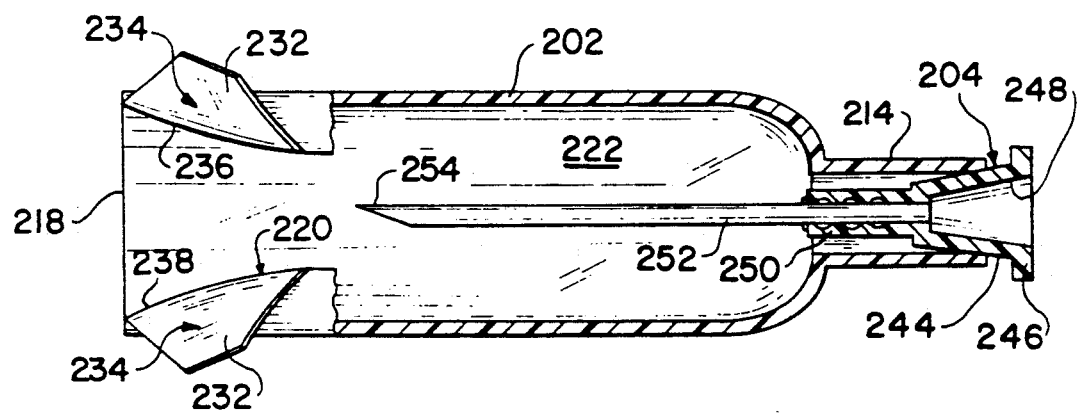
FIG. 1B shows a partial cross-sectional view and partial bottom view taken along line B—B in FIG. 1A.
Figure 1C:
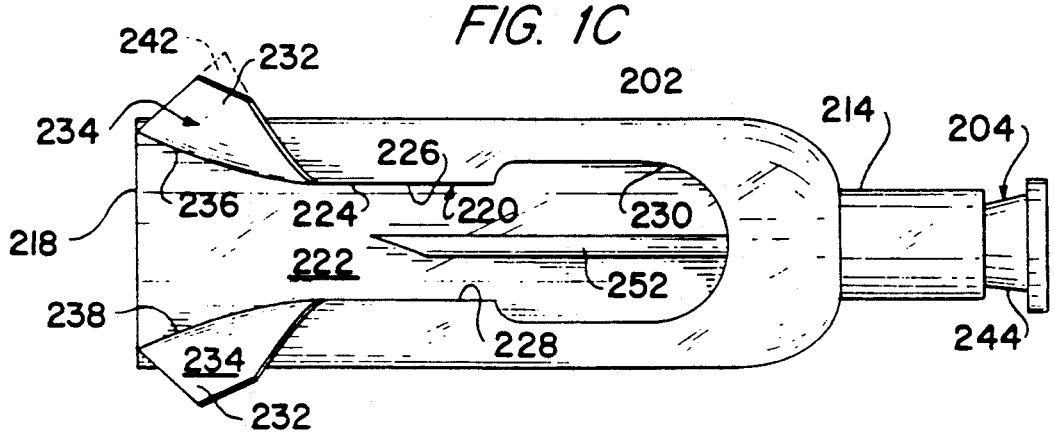
FIG. 1C shows a bottom view of the present invention.

As illustrated in FIGS. 1A–1C, sheath 202 includes an open end 218, slot 220, and hollow interior 222. As best shown in FIG. 1C slot 220 features channel section 224 defined by the generally straight line edge sections 226 and 228. Channel 224 opens at one end into aperture 230 which has a transverse width slightly larger than the transverse width of channel 224 such that an intravenous fluid line which is slid along channel 224 becomes releasably locked in place within aperture 230. This arrangement is described in greater detail below.

At the opposite end of channel 224 is a pair of wing sections 232 which are preferably formed by injection molding or by folding portions of sheath 202 at the end region of slot 220 outwardly in a manner which provides a pair of smooth, planar runner surfaces 234. Planar runner surfaces 234 preferably have a width which is about 1.5 to 4 times the average thickness of sheath 202 and more preferably 2 times the average thickness.

Wing sections 232 are folded or molded to extend outwardly from lines 236 and 238, respectively. As illustrated in FIG. 1A, line 236 slopes upwardly from the end of channel 226 to a point P positioned in upper portion 212 of sheath 202. In a preferred embodiment point P is positioned within the range defined by the mid-third 240 of the height h of upper portion 212. Moreover, to avoid undue outward extension and sharp edge corners a portion 242, shown in dashed lines in FIG. 1C is removed from each wing section. FIG. 1A illustrates sloping angle which preferably lies between about 25° to 40° and more preferably is 30°.

As shown in FIG. 1B connecting means 204 includes cupshaped member 244 having outwardly extending flange 246 and tapered recess 248 which together provide suitable means for connecting protective apparatus 200 to a suitable fluid source such as a syringe or intravenous tubing. Connecting means 204 further includes extension 250. Extension 250 receives in locking fashion one end of cannula 252 which has its scarf end 254 positioned on the central axis within hollow interior 222. The length of the centrally positioned cannula 252 is such that end 254 lies between the ends of channel 224 and behind wing extensions 232.

Figure 1D:
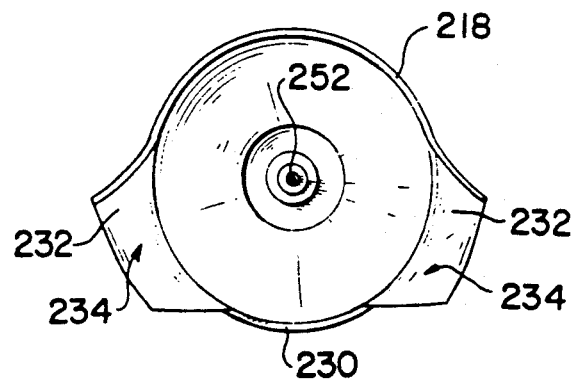
FIG. 1D shows a front view of the present invention.

FIG. 1D illustrates open end 218 of protective sheath 202 as well as the downwardly tapering wing-shaped runners 234.

Figure 1E:
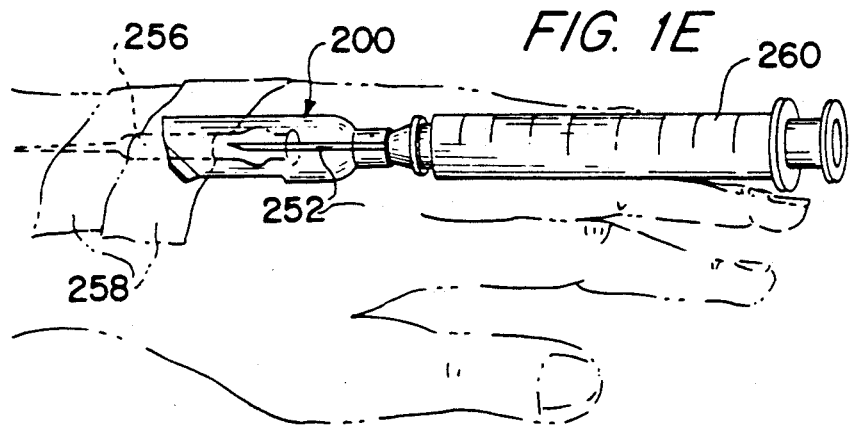
FIG. 1E shows the present invention just prior to being in operative position with respect to an implanted cannula.

FIG. 1E show protective apparatus 200 immediately prior to being placed into operative position with respect to an implanted cannula 256 held in position with tape strips 258. As illustrated, cannula 252 is received within a receptive port forming part of implanted cannula assembly 256. Syringe 260 is connected at its forward end to connecting means 204 and the combination is slid into position over tape 258.

Figure 1F:
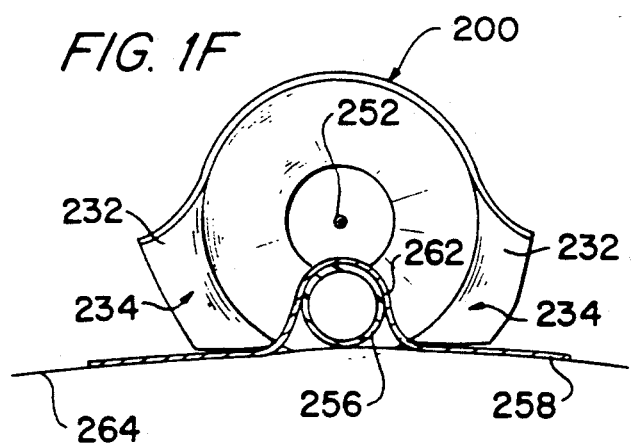
FIG. 1F shows a frontal view of the protective sheath positioned over tape holding an implanted cannula in position.

FIG. 1F shows how runners 234 easily slide over the tent portion 262 of tape strip 258 that holds in place implanted cannula assembly 256. The smooth, planar surface 234 is adapted to slide over tape strip 258 without disrupting strip 258 from its adhesive position on skin surface 264. FIG. 1F represents the initial insertion of protective sheath 200 prior to cannula 252 being inserted into the receptive port of implanted cannula assembly 256.

Figure 1G:
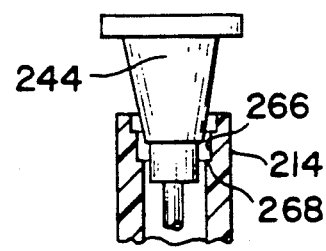
FIG. 1G shows the connection means and neck extension of the present invention just prior to being secured to one another.
Figure 1H:
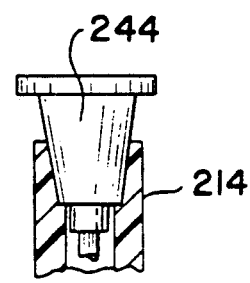
FIG. 1H shows the positioning of the connecting means and neck extension after being ultrasonically welded to one another.

FIGS. 1G and 1H illustrate the arrangement of cup-shaped member 244 with respect to neck extension 214 just prior to ultrasonic welding and after ultrasonic welding has taken place. In a preferred embodiment ultrasonic welding is performed in the shear weld fashion wherein a shear joint is formed between the two connected members following softening of the exterior of cup-shaped member 244 and the raised section 266 which places cup-shaped member in an interference fit arrangement during the welding operation. Shoulder portion 268 provides a stop edge upon which cup-shaped member rests following completion of the welding operation. To achieve the best securement, both the cup-shaped member and neck extension are of the same material or of materials having less than a 20° F. difference in their melting point.

Figure 3:
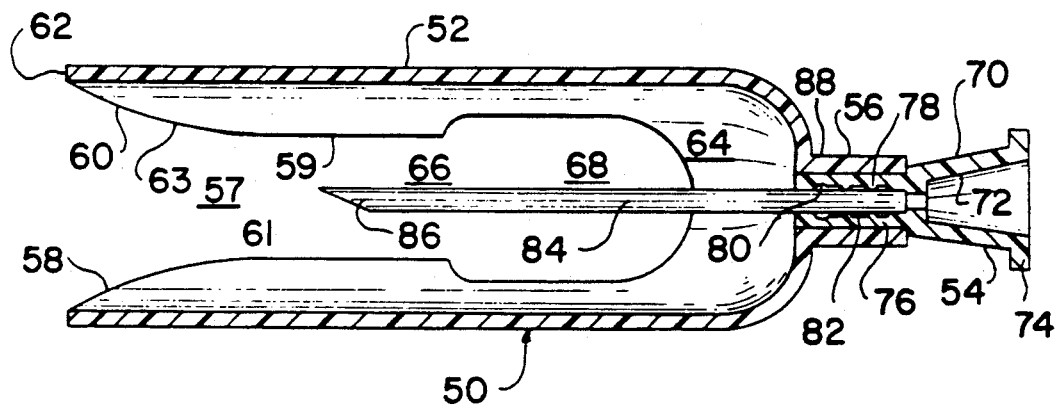
FIG. 3 illustrates a cross-sectional view taken along line A—A in FIG. 2.

FIG. 3 illustrates an alternate arrangement wherein the neck extension is ultrasonically welded to extension 250 rather than cup-shaped member 244.

An alternate, but less preferable, manner of attachment would include the use of an adhesive to secure the connecting means to the neck extension or a butt or energy direct weld.

Figure 9:
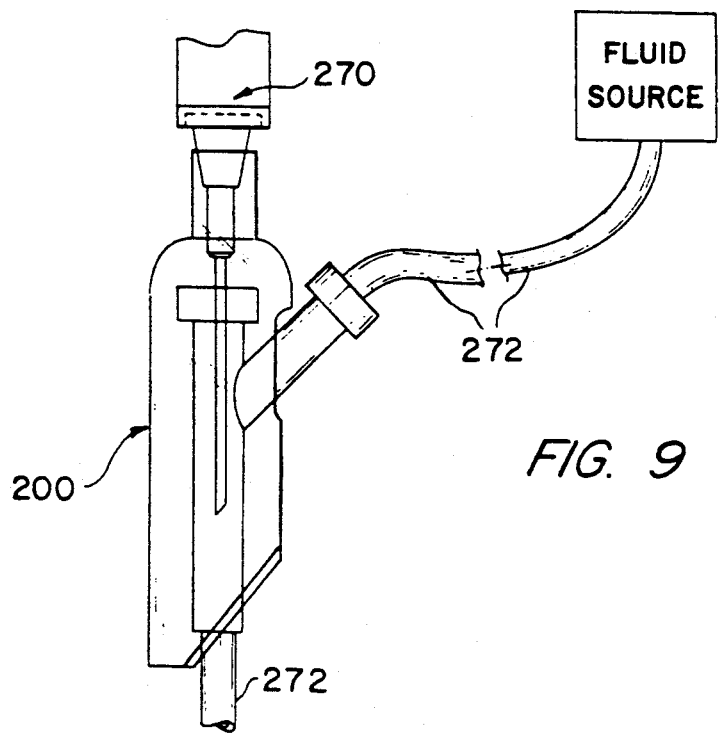
FIG. 9 shows the first embodiment of the present invention in position over an intravenous Y-junction.
Figure 12:
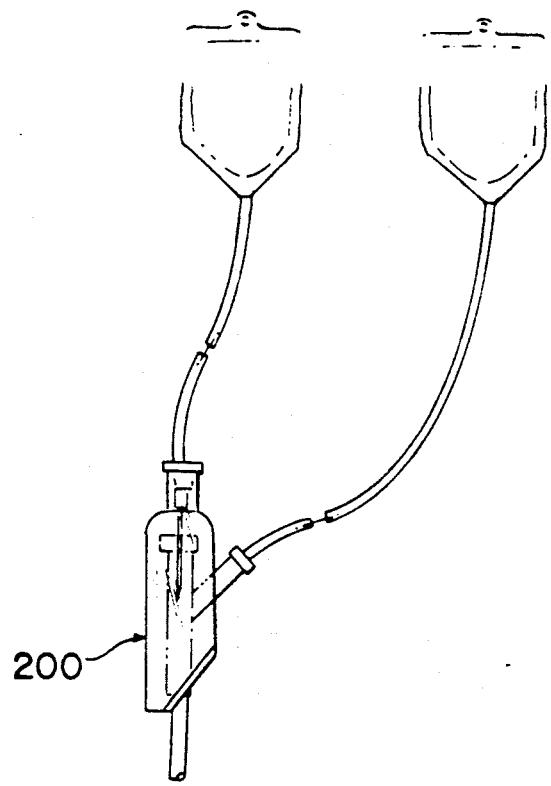
FIG. 12 shows the first embodiment shown in operating position on an intravenous piggy back system.

FIG. 12, and in greater detail FIG. 9, show protective sheath 200 in its subordinate use as a protective shield for use with an intravenous tubing system. As shown, fluid introduction device 270, which typically is a syringe or the end of an auxiliary line, is attached at the connecting end of protective apparatus 200. As shown in FIG. 9, elongated aperture 230 (FIG. 1C) receives fluid line 272 and the channel section 224, which opens into aperture 230, has a smaller with that the diameter of line 272 such that deformation of the sheath and/or fluid line occurs during passage of fluid line 272 in channel 224.

Figure 2:
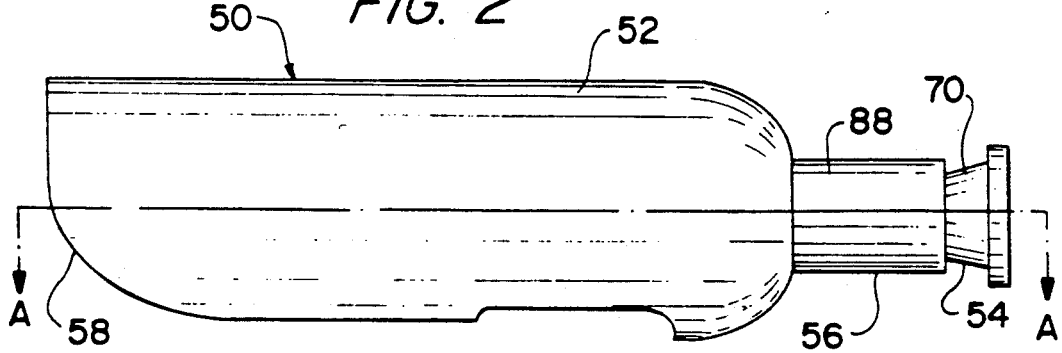
FIG. 2 shows a side view of a second embodiment of the present invention.

FIG. 2 shows a second embodiment of the present invention featuring protective apparatus 50 having protective sheath 52 and connecting means 54 secured to the connecting end 56 of sheath 52.

FIG. 3 shows slot 57 formed in a lower portion of protective sheath 52. Slot 57 extends from open end 62 of protective sheath 52 inwardly towards connecting end 56. Slot 57 is defined by edge 63 which defines curved sections 58, 60, planar sides 59, 61 defining channel 66, and edge section 65 defining elongated aperture 68. Elongated aperture 68 preferably extends for about 25 to 35% of the entire length of the sheath. Connecting means 54 includes cup-shaped member 70 having tapered recess 72 and luer flange 74. Extending off the base of cup-shaped member 70 is cylindrical extension 76. Cylindrical extension 76 includes recess 80 as well as projections 78 defining ringed recesses 82 therebetween. Cannula 84 has its scarf end 86 positioned within hollow interior 64 which is defined by the interior surface of protective sheath 52. The opposite end of cannula 84 is received within recess 80 and maintained centrally positioned by projections 78. In a preferred embodiment, the cannula is retained within recess 80 by way of an adhesive retained within ringed recesses 82.

The connecting end 56 of protective sheath 52 includes neck extension 88 which surrounds and is attached to cylindrical extension 76. A suitable manner for attaching neck extension 88 to cylindrical extension 76 includes the ultrasonic welding of the two together.

FIG. 7 shows a prospective view of the open end 62 of protective sheath 52. FIG. 7 also illustrates curved sections 58, 60 defining a portion of slot 57. Curved sections 58, 60 are shown to be in mirror image arrangement equally spaced about center line 90. Curved sections 58, 60 feature a smooth, planar edge surface which provide protective sheath 52 with sleigh-like runners extending from the open end back towards the connecting end of the protective sheath. The planar edge surface defining curved sections 58, 60 are arranged transverse to view line V representing a line of sight extending directly into the open end of protective sheath 52.

Figure 4:
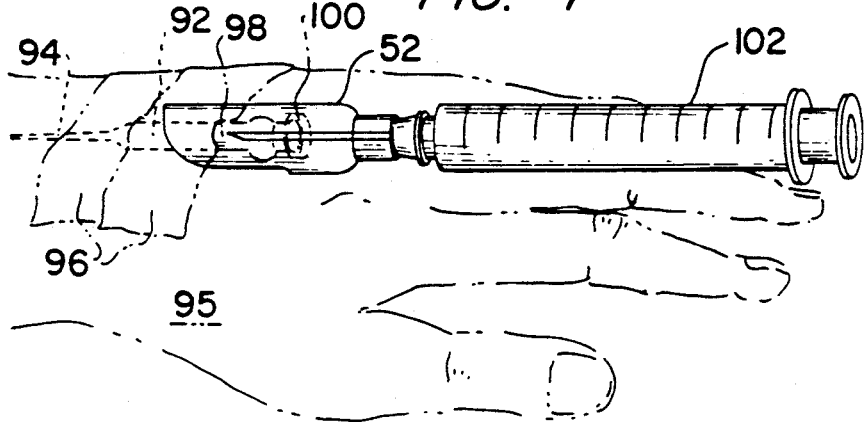
FIG. 4 shows the second embodiment positioned over an implanted intravenous cannula assembly and in connection with a syringe.

FIG. 4 illustrates protective sheath 52 being placed into operating position with respect to implanted intravenous cannula assembly 92 featuring flexible cannula 94 implanted under the patient's skin as well as tape sections 96. Intravenous cannula assembly 92 further comprises extension conduit 98 having receiving port member 100 attached to it. Protective sheath 52 is also shown in FIG. 4 to be connected with a syringe 102.

FIGS. 5A, 5B and 6 illustrate the sleigh-like runners 58, 60 in operation with respect to the upper surface of the patient's hand 95 as well as tape 96. As shown in FIGS. 5A and 5B, runners 58, 60 provide a smooth transition as the protective sheath is forced along the upper portion of the patient's hand and over tape 96.

FIG. 6 further illustrates the manner in which the runners as well as the remainder of the slot provide for a smooth transition over the tent-shaped section 102 of the portion of tape 96 extending about conduit 98. FIG. 6 further illustrates planar contact areas 104, 106 which exist between runners 58, 60 and tape 96.

This embodiment can be inserted over the auxiliary branch of an intravenous Y-junction in a manner similar to that which is shown in FIG. 9 for the first embodiment. In a position such as that shown in FIG. 9, protective sheath 52 protects a person from being stuck by a cannula upon insertion of the cannula into the auxiliary branch. Protective sheath 52 would be connected with a fluid insertion device which could include a syringe or the distal end of an intravenous tube connected to an auxiliary fluid source of the piggy back intravenous system. In securing the cannula into the auxiliary branch of a Y-junction, the slot 57 is aligned such that channel sides 59, 61 are laterally spaced about the main line of the intravenous tube system. The width of the channel is preferably made less than the diameter of the main line such that, when the protective sheath 52 is pushed over the auxiliary branch, the main line slides along channel 66 while deforming sides 59, 61 until the main line is received within elongated aperture 68 and sides 59, 61 snap back into their non-deformed position. The sliding arrangement between the main line and channel 66 also helps to ensure proper insertion of cannula 84 into auxiliary 108.

Figure 10:
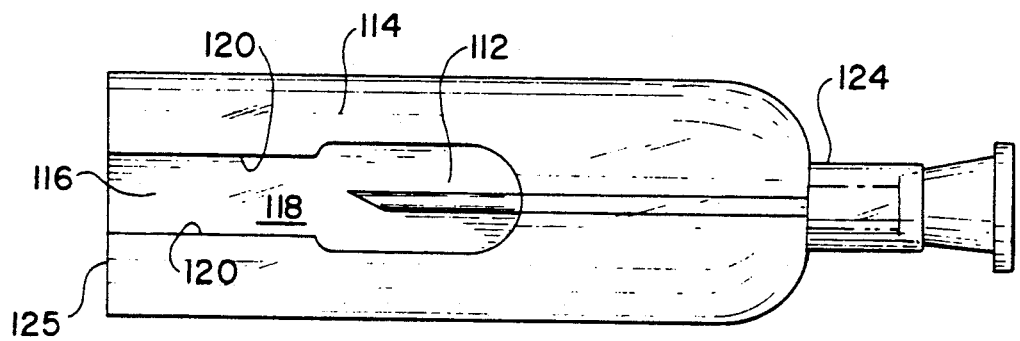
FIG. 10 shows a bottom view of a third embodiment of the present invention.
Figure 11:
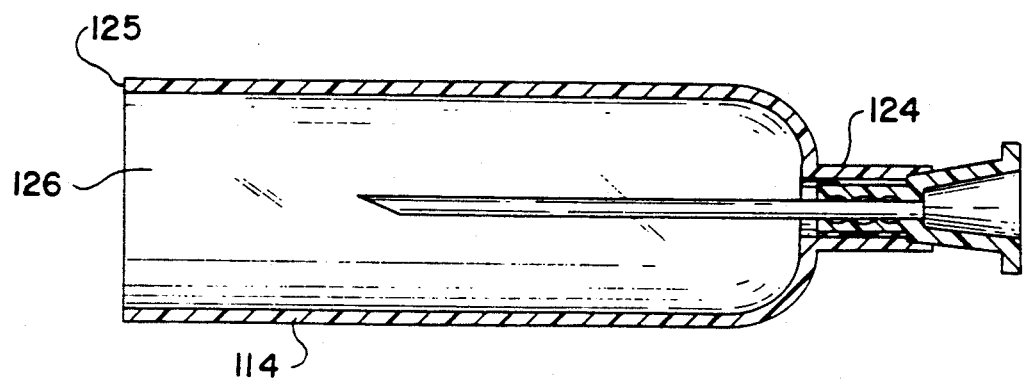
FIG. 11 shows a cross-sectional of that which is shown in FIG. 10.

FIGS. 10 and 11 illustrate a third embodiment of the invention particularly suited for protecting a person inserting a cannula into an auxiliary branch of an intravenous system's Y-junction. Protective sheath 114 is provided with a keyhole-shaped slot 116 having channel 118 defined by side edges 120. Aperture 122 is formed in protective sheath 114 so as to open into the end of channel 118 which is closest to connecting end 124. Protective sheath 114 includes edge section 124 defining open end 126. The cannula and connecting means arrangement described for the first embodiment is preferably the same for the third embodiment and thus, further description is not required. Moreover, the channel 118 and aperture 122 are dimensioned in a manner similar to that described for the first and second embodiments wherein channel 118 has a width less than the main line of an intravenous system and aperture 122 has a transverse width which is the same or slightly larger than the main lines. With this arrangement, the main line is releasably locked within aperture 122 following insertion of the main line through channel 118. Forming the sheath of a flexible material provides for deformation of the channel during the sliding through of the main line and the sheath is adapted to snap back into place following placement of the main line in aperture 122.

Figure 14:
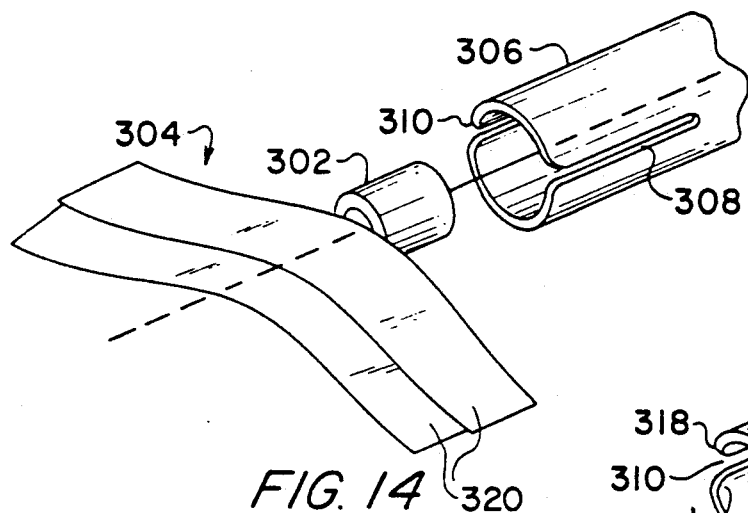
FIG. 14 shows another embodiment of the present invention just prior to insertion over the reception port of an implanted intravenous cannula assembly.
Figure 14A:
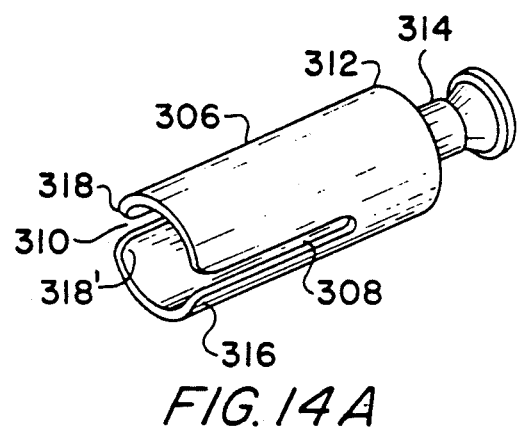
FIG. 14A shows a perspective view of the embodiment of FIG. 14.
Figure 14B:
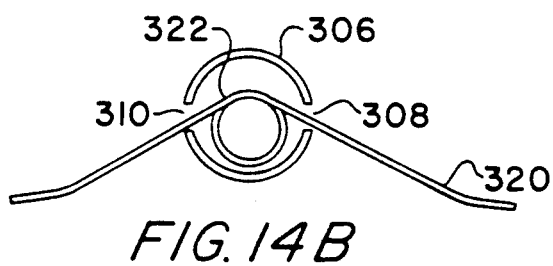
FIG. 14B shows the embodiment of FIG. 14 in position over a tent-shaped tape strip.

FIG. 14 shows an additional embodiment of the present invention in position for insertion over reception port 302 of implanted cannula assembly 304. The embodiment of FIG. 14 features protective sheath 306. Protective sheath 306, as shown in FIG. 14 and 14A, features a pair of slits, 308, 310 extending for over a third of the length of main body 312 of protective sheath and more preferably for about 45 to 55% of the length of main body 312 or about 40 to 50% of the entire length of protective sheath 306. Neck extension 314 and main body 312 combine together in forming protective sheath 306. Protective sheath 306 further includes curved inlet portions 316, 316' and 318, 318' which combine together to facilitate insertion of tape strips 320. FIG. 14B illustrates tent-shaped tape portion 322 in position within slits 308,310.

Figure 14C:
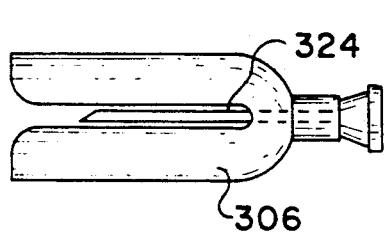
FIG. 14C shows the embodiment of FIG. 14 with a cannula.

FIG. 14C illustrates cannula 324 and its position with respect to protective sheath 306.

Figure 14D:
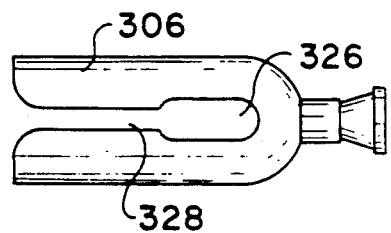
FIG. 14D shows the embodiment of FIG. 14 with one of the slits modified.

FIG. 14D illustrates a modification of the embodiment of FIG. 14A wherein one of the opposed slits includes an elongated aperture 326 in combination with a channel section 328 which together facilitates use of protective sheath 306 at a Y-site of an intravenous system.

Figure 15:
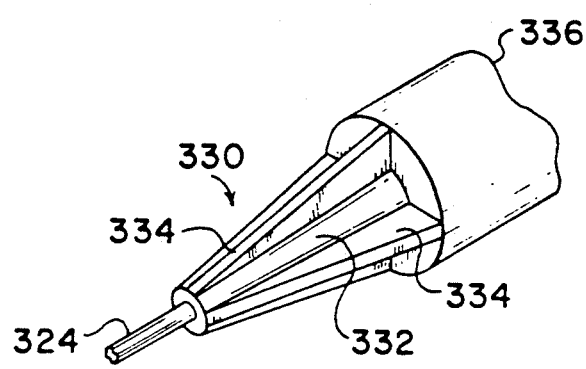
FIG. 15 shows, in cut away, a cannula assembly with web extension forming part of a projection member supporting a cannula.
Figure 16A:
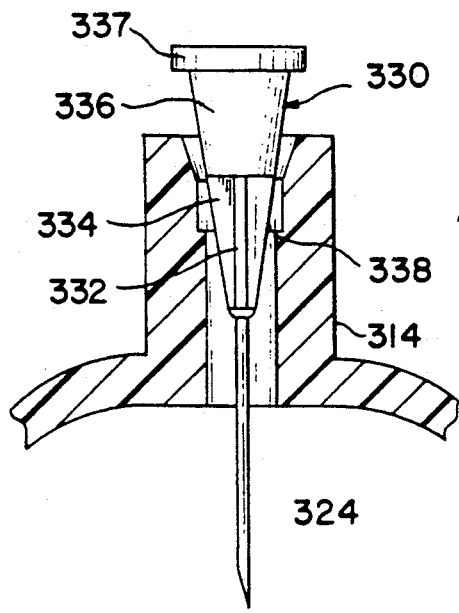
FIG. 16A shows a partially cut away cross-sectional view of the cannula assembly depicted in FIG. 15 in position with a neck extension of a protective sheath.
Figure 16B:
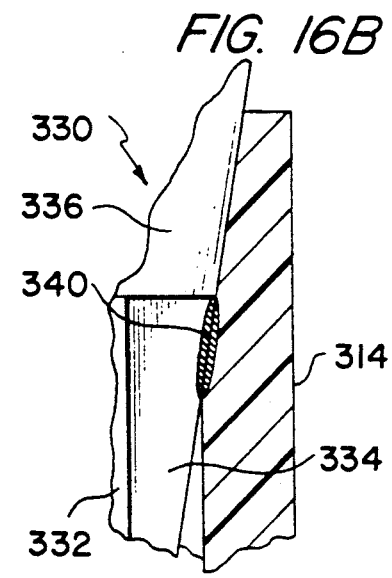
FIG. 16B shows in greater detail the ultra sonic weld holding the webs of the cannula assembly to the neck extension.

FIGS. 15, 16A and 16B illustrate the ultrasonic welding of cannula assembly 330 within neck extension 314. As shown, cannula assembly 330 includes cannula 324, projection member 332, webs 334 and hub 336. Hub 336 includes flange extension 337 as shown in FIG. 16A. Raised section 338 of neck extension 314 comes together with webs 334 so as to provide contacting surfaces for forming ultra sonic weld 340.

Figure 17:
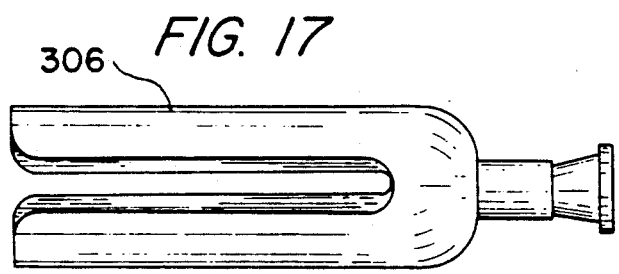
FIG. 17 shows the embodiment of FIG. 14 with one of the slits widened.
Figure 18:
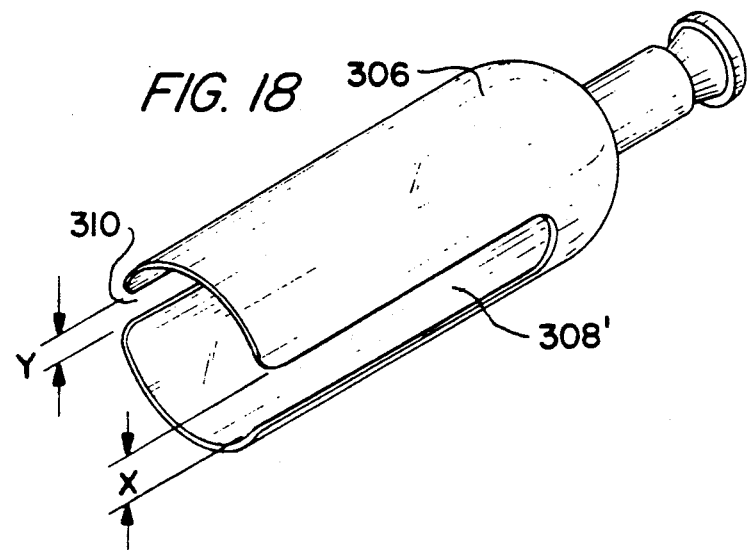
FIG. 18 shows the embodiment of FIG. 17 in perspective.

FIGS. 17 and 18 show protective sheath 306 with a modified slit 308' and "normal" slit 310. Modified slit 308' is made wider than slit 310 so as to facilitate use of protective sheath 306 at a Y-site of an intravenous system. Preferably width is about 0.2 to 0.3 of an inch and width Y is about ⅛ of an inch.

Figure 19A:
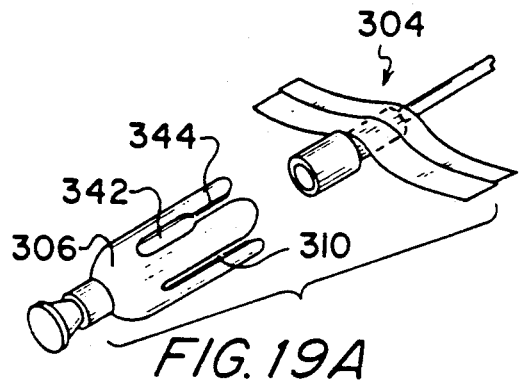
FIG. 19A shows another embodiment of the present invention just prior to insertion over the reception port of an implanted intravenous cannula assembly.
Figure 19B:
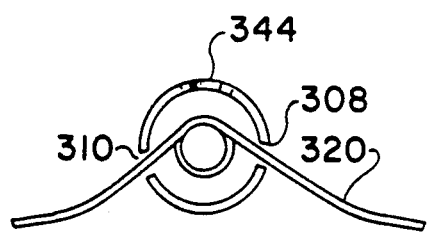
FIG. 19B shows the protective sheath of FIG. 19A in position over the tape strips holding the reception port in position.

FIG. 19A reveals another modification of sheath 306 wherein, in addition to slits 308 and 310, there is provided elongated aperture 342 and channel 344. FIG. 19.A further illustrates protective sheath 306 just prior to being inserted over implanted cannula assembly 304. FIG. 19B illustrates tape sections 320 having been inserted into slits 308 and 310.

Figure 19C:
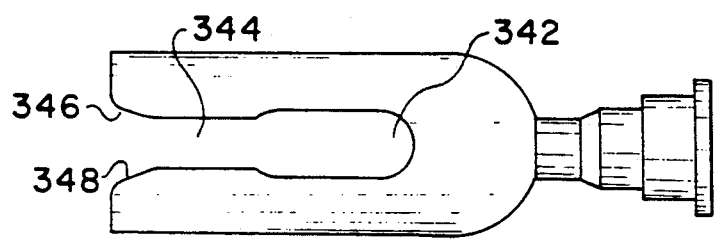
FIG. 19C shows a planar view taken along line B—B in FIG. 19E of the protective sheath shown in FIG. 19A.

FIG. 19C illustrates, in planar view, protective sheath 306 having channel 344 and elongated aperture 342. FIG. 19C also shows channel 344 having curved inlet sections 346 and 348 which are useful upon insertion of the tape strips within channel 344 and one of the two slits 308 and 310 as opposed to only between slits 308 and 310. Channel 344 and elongated aperture 342 combine to represent about 45 to 55% of the length of the main body of protective sheath 306 and more preferably about 50% with the ratio of aperture length to channel length being from about 1:1 to 1.5:1. The slits extend inwardly for about the same length as that described for the channel and aperture combination.

Figure 19D:
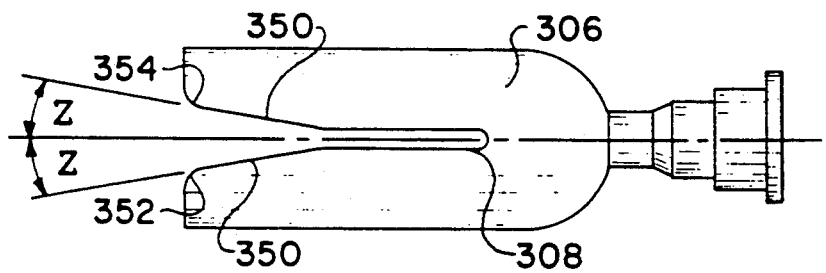
FIG. 19D shows a side view taken along line A—A in FIG. 19E of the protective sheath shown in FIG. 19A.

FIG. 19D shows a side view of the embodiment shown in FIG. 19D wherein slits 308 and 310 are modified to include tapered sections 350 extending from curved inlet sections 352, 354. The angle of incline of tapered sections 350 is represented by Z which is preferably about 6 to 10%.

Figure 19E:
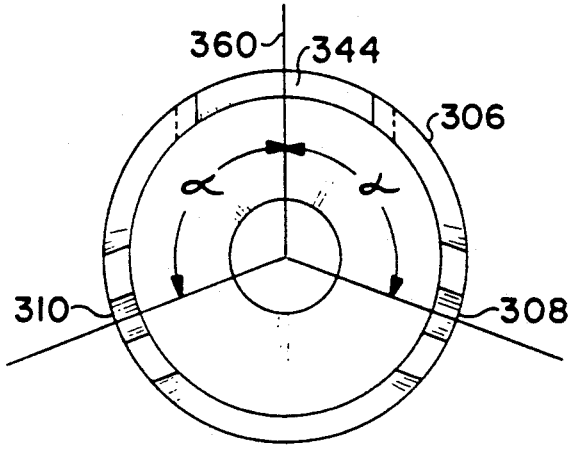
FIG. 19E shows a front view taken along line C—C in FIG. 19C of the protective sheath shown in FIG. 19A.

FIG. 19E shows a front view of the open end of protective sheath 306. The positioning of the slits 308 and 310 is preferably within the range of 90° C. to 120° C. and verticle center line 360 as represented by α.

Figure 20:
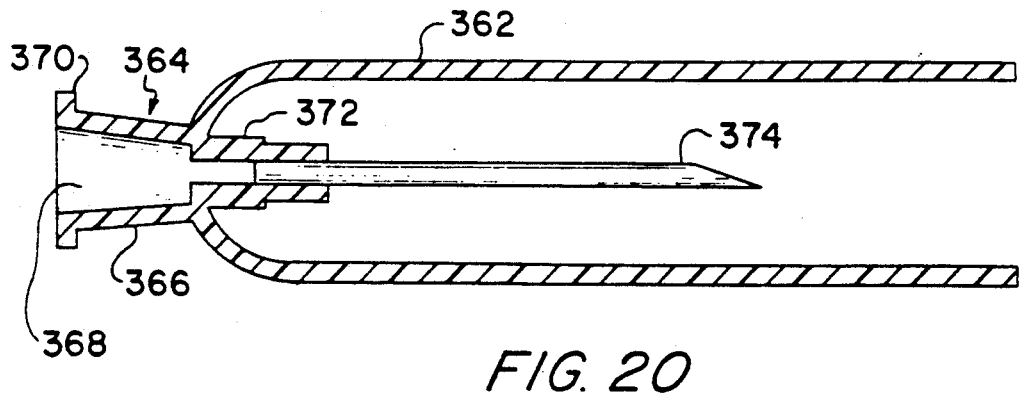
FIG. 20 shows a cross-sectional view of a protective sheath which is integrally molded with the connecting means.

FIG. 20 shows an alternate embodiment of the present invention with protective sheath 362 being integrally molded with connecting means 364. Connecting means 364 includes cupshaped member 366 with female recess 368 for receiving the male counterpart of a fluid insertion device (not shown). Flange 370 also forms part of connecting means 364 and provides a locking function with respect to the male counterpart of a fluid insertion device. Connecting means 364 further includes stepped projection member 372 extending into the hollow interior of sheath 362. Cannula 374 can be insert molded, adhered or a combination of both into a recess provided in stepped projection member 372.

Figure 21A:
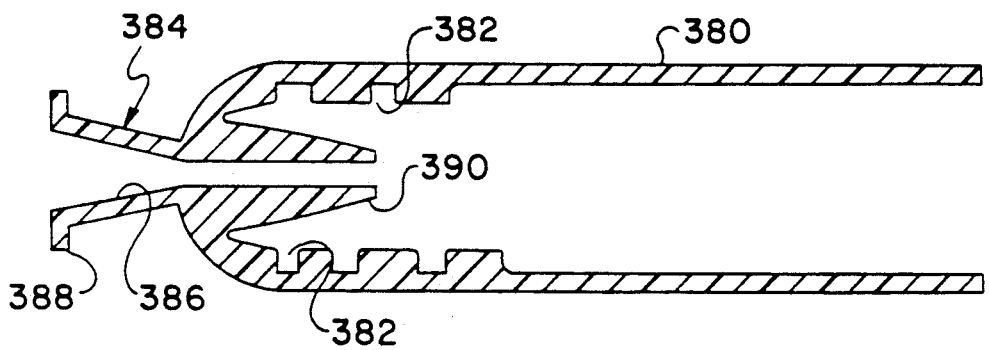
FIG. 21A shows a cross-sectional view of an alternate embodiment of the present invention which is suited for receipt of a releasable locking cannula assembly.

FIG. 21A shows an alternate embodiment of the present invention featuring protective sheath 380 having recess groove 382 formed on the interior surface of sheath 380. Connecting means 384 includes a cup-shaped member with tapered recess 386 and flange 388 so as to provide a female lock arrangement. Extending inwardly into the hollow interior of sheath 380 is tapered projection member 390.

Figure 21B:
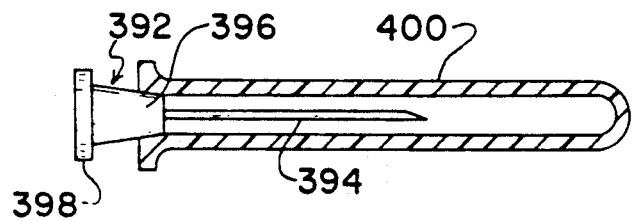
FIG. 21B shows a releasable locking cannula assembly covered by a protective guard.

FIG. 21B shows cannula assembly 392 having cannula 394, hub 396 and flange 398. Protective guard 400 is inserted over cannula 394 and is releasably connected at its open end to hub 396.

Figure 21C:
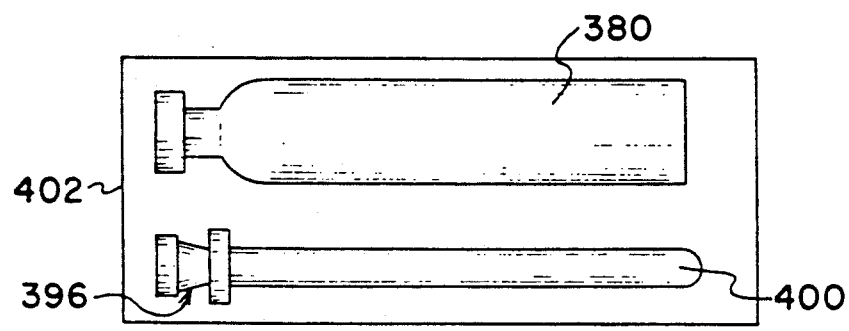
FIG. 21C shows a casing for holding a protective sheath, guard and cannula prior to use.

FIG. 21C shows packaging 402 for holding a protective sheath 380, cannula assembly 392, and guard 400. Package 402 can include a molded stiff plastic body with a clear plastic seal thereover.

Figure 21D:
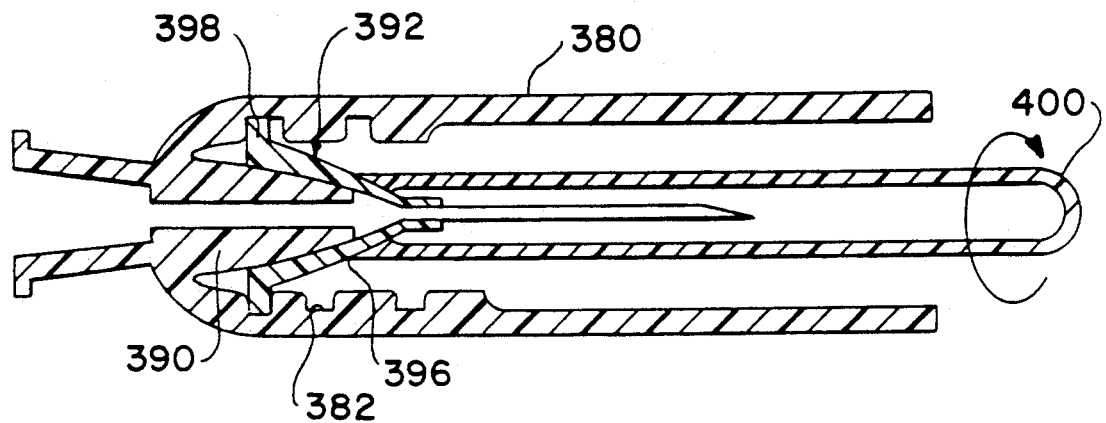
FIG. 21D shows in cross-section the cannula assembly and protective guard in locked position.

FIG. 21D reveals the locking arrangement between sheath 380, cannula assembly 392 and protective guard 400. As shown, flange 398 is releasably locked in position within groove 382 by a twisting action of guard 400 and the attached cannula assembly 392. Tapered projection member 390 is arranged so as to frictionally come in contact with the surface defining the tapered recess formed in hub 396.

Figure 21E:
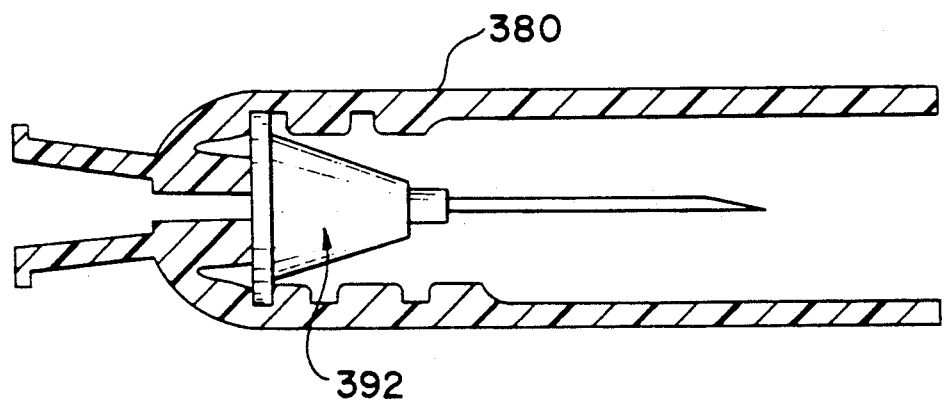
FIG. 21E shows the cannula assembly in locked position with the protective guard removed.

The combination of flange 398 in groove 382 and projection member 390 within hub 396 ensures a secure, sealed fit between cannula assembly 392 and sheath 380. When the protective sheath and attached cannula assembly are to be utilized, protective guard 400 can be removed by drawing it out away from the open end of sheath 380. FIG. 21E depicts having cannula assembly 392 in operating position and protective guard 400 removed.

While the device and method of the present invention have been described with regard to certain embodiments and exemplifications thereof, further variations thereof will be apparent to those skilled in the art and are intended to be encompassed by the claims appended hereto. For example, the inclusion of planar strips attached at their midsection and in a perpendicular relationship to the sleigh-like runners to enhance the sliding surface is a contemplated modification of the present invention (see FIG. 6, 300).

What is claimed is:

1. A method for avoiding needle sticks during insertion of a needle into and removal of needle out of an implanted intravenous assembly, comprising:

aligning a protective sheath having a pair of slits formed therein such that a needle covered by said protective sheath is generally centered with respect to a reception port forming part of the implanted intravenous assembly, aligning the slits formed in said protective sheath with a tape strip holding down the implanted intravenous assembly such that said slits are adapted to receive the tape strip therein;

forcing said protective sheath forward so as to have the reception port positioned within a hollow interior of said protective sheath, the needle extending into the reception port, and the tape strip retained within said pair of slits formed in said protective sheath.

* * * * *